United States Patent
Al-Harthi

(10) Patent No.: US 10,688,152 B2
(45) Date of Patent: Jun. 23, 2020

(54) COMPOSITIONS AND METHODS FOR TREATING A VIRAL INFECTION

(71) Applicant: RUSH UNIVERSITY MEDICAL CENTER, Chicago, IL (US)

(72) Inventor: Lena Al-Harthi, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 374 days.

(21) Appl. No.: 15/510,902

(22) PCT Filed: Sep. 18, 2015

(86) PCT No.: PCT/US2015/050922
§ 371 (c)(1),
(2) Date: Mar. 13, 2017

(87) PCT Pub. No.: WO2016/048824
PCT Pub. Date: Mar. 31, 2016

(65) Prior Publication Data
US 2019/0083572 A1 Mar. 21, 2019

Related U.S. Application Data

(60) Provisional application No. 62/053,462, filed on Sep. 22, 2014.

(51) Int. Cl.
*A01K 67/027* (2006.01)
*A61K 31/4164* (2006.01)
*A61K 31/4178* (2006.01)
*A61K 31/421* (2006.01)
*A61K 31/4439* (2006.01)
*A61K 38/17* (2006.01)
*A61P 31/22* (2006.01)
*A61P 31/18* (2006.01)
*A61K 35/17* (2015.01)

(52) U.S. Cl.
CPC .......... *A61K 38/1709* (2013.01); *A61K 35/17* (2013.01); *A61P 31/18* (2018.01); *A61P 31/22* (2018.01)

(58) Field of Classification Search
CPC .......... A01K 2217/075; A01K 2217/15; A01K 2217/203; A01K 2227/105; A01K 2267/0331
See application file for complete search history.

(56) References Cited

U.S. PATENT DOCUMENTS

2006/0171931 A1* 8/2006 Rudnicki ............... A61K 35/34
424/93.7

FOREIGN PATENT DOCUMENTS

| WO | WO 2008/016994 | 2/2008 |
| WO | WO 2013/040309 | 3/2013 |
| WO | WO 2013/129929 | 9/2013 |
| WO | WO2013129929 | * 9/2013 |

OTHER PUBLICATIONS

Richards et al., "Porcupine Is Not Required for the Production of the Majority of Wnts from Primary Human Astrocytes and CD8+ T Cells", PLOS One, 2014, 9(3):1-6.*
Richards et al., "Porcupine Is Not Required for the Production of the Majority of Wnts from Primary Human Astrocytes and CD8+ T Cells" Mar. 19, 2014 (Mar. 19, 2014) PLoS One, Mar. 2014, vol. 9 Issue 3, pp. 1- 6, p. 3 col. 1 para 3, in 3-5.
International Search Report and Written Opinion for PCT/US2015/050922 dated Dec. 11, 2015, 9 pgs.
International Preliminary Report on Patentability for PCT/US2015/050922 dated Apr. 6, 2017, 8 pgs.
Extended European Search Report for EP 15 84 3708 dated Mar. 23, 2018, 8 pgs.
Jorg Van Loosdregt et al: 11 Canonical Wnt Signaling Negatively Modulates Regulatory T Cell Function, Immunity., vol. 39, No. 2, Aug. 1, 2013 (Aug. 1, 2013), pp. 298-310.

* cited by examiner

*Primary Examiner* — Barry A Chestnut
(74) *Attorney, Agent, or Firm* — Barnes & Thornburg LLP

(57) ABSTRACT

One aspect of the present invention provides methods of treating a viral infection in a subject including administrating a therapeutically effective amount of at least one Wnt ligand protein selected from Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 and Wnt16. In one embodiment, the subject is a human and the infection is a human immunodeficiency virus infection. Another aspect provides drug combinations for treating viral infections.

14 Claims, 4 Drawing Sheets

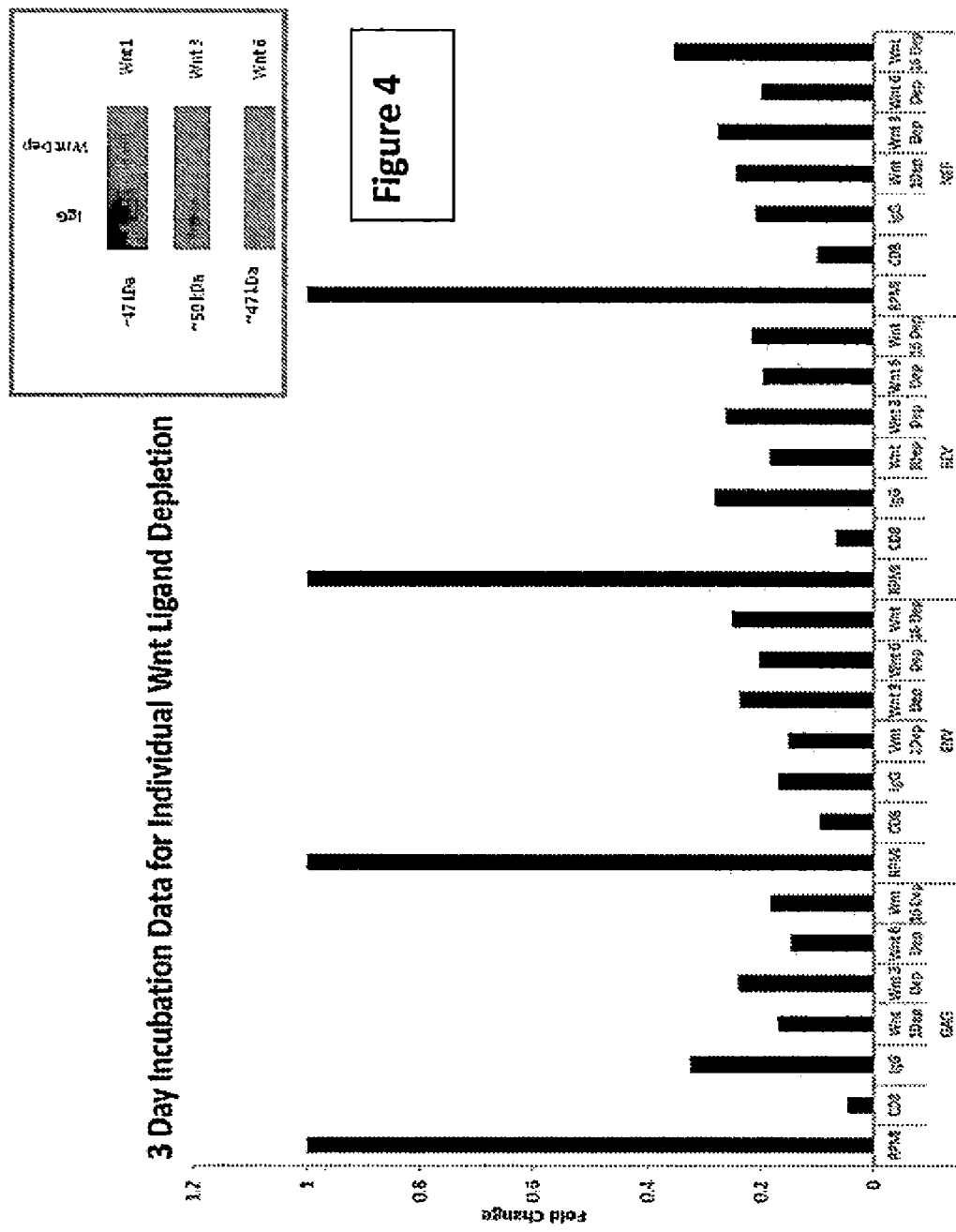

COMPOSITIONS AND METHODS FOR TREATING A VIRAL INFECTION

CROSS-REFERENCE TO RELATED APPLICATIONS

This application is a National Stage of PCT/US2015/050922, filed Sep. 18, 2015, which claims the benefit of the filing date of U.S. Provisional Patent Application No. 62/053,462, filed Sep. 22, 2014, the contents of which applications are hereby incorporated by reference.

FEDERALLY SPONSORED RESEARCH OR DEVELOPMENT

This invention was made with Government support under Grant No. R01 NS060632, awarded by the National Institutes of Health. The Government has certain rights in the invention.

TECHNICAL FIELD

The present invention generally relates to methods and compositions for treating a viral infection in a subject, and in particular to methods and compositions for treating a human immunodeficiency virus infection.

BACKGROUND

The human immunodeficiency virus (HIV) causes acquired immunodeficiency syndrome (AIDS), a condition in humans in which progressive failure of the immune system allows life-threatening opportunistic infections and cancers to thrive. Infection with HIV occurs by the transfer of blood, semen, vaginal fluid, pre-ejaculate, or breast milk. Within these bodily fluids, HIV is present as both free virus particles and virus within infected immune cells.

HIV infects vital cells in the human immune system such as helper T cells (specifically CD4+ T cells), macrophages, and dendritic cells. HIV infection leads to low levels of CD4+ T cells through a number of mechanisms, including apoptosis of uninfected bystander cells, direct viral killing of infected cells, and killing of infected CD4+ T cells by CD8 cytotoxic lymphocytes that recognize infected cells. When CD4+ T cell numbers decline below a critical level, cell-mediated immunity is lost, and the body becomes progressively more susceptible to opportunistic infections.

A number of therapeutic agents have been used to treat AIDS. Such agents include reverse transcriptase inhibitors (such as AZT), protease inhibitors (such as Indinavir) and integrase inhibitors (such as raltegravir.) However, although such agents have been shown to be affective, at least in the short term, their use may result in numerous side effects, for example, kidney problems and emergence of resistant viruses. As a result of these limitations, the development of new anti-HIV drugs having an alternative mechanism of action offers certain advantages.

Wnt ligands are small highly conserved glycoproteins consisting of 19 members approximately 35-50 kDa in size. They are produced by a variety of cell types and once secreted; can bind one of 10 Frizzled (Fzd) receptors on their target cells. Depending on the Wnt/Fzd combination, the result can be either a signal transduction cascade that is β-catenin-dependent (canonical pathway) or β-catenin independent. In the nucleus, β-catenin functions as a transcriptional/co-regulator where it binds to members of the LEF/TCF transcription factors to regulate gene expression. At the cell membrane, β-catenin functions as an adhesion protein contributing to cell structure and to cell-to-cell communication.

CD8+ T cells secrete a yet to be identified entity referred to as CD8 antiviral factor (CAF) that inhibits LTR-driven transcription of the HIV provirus in CD4+ T cells. The identity of CAF has remained elusive for over 30 years. Several key properties of CAF are known. CAF suppresses HIV replication at the level of transcription, it is stable at high temperature (56 for 20 min or 100 at 10 min) and low pH (2-8), and is secreted from activated CD8 T cells.

BRIEF SUMMARY

One aspect of the present invention provides a method of treating a viral infection. The method includes administering to a subject in need of such treatment a composition including a therapeutically effective amount of at least one Wnt ligand protein from the group of Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 and Wnt16. In another embodiment the Wnt ligand protein is selected from the group of Wnt1, Wnt2B, Wnt3, Wnt5B, Wnt8A, Wnt9A, Wnt9B, Wnt10A, Wnt10B and Wnt16. The composition can also include at least one pharmaceutically acceptable carrier, diluent or excipient.

The method may also include the administration of a therapeutically effective amount of at least two Wnt ligand proteins from the group consisting of Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 and Wnt16. In another embodiment, the method includes the administration of at least two Wnt ligand proteins selected from the group consisting of Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 and Wnt16.

In one embodiment, the viral infection is a human immunodeficiency virus infection. The infection can be caused by a HIV virus that is resistant to a reverse transcriptase inhibitor or a protease inhibitor. In another embodiment, the viral infection is a Cytomegalovirus infection, a Hepatitis C virus (HCV) infection or a Sendai-Virus infection.

Another aspect of the present invention provides a drug combination including at least two Wnt ligand proteins selected from the group consisting of Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 and Wnt16. In one embodiment, the drug combination is a synergistic drug combination. The drug combination can also include a pharmaceutically acceptable carrier, diluent or excipient.

BRIEF DESCRIPTION OF THE DRAWINGS

FIG. 4 is a graph showing the depletion of Wnt ligands leads to an abrogation of CAF activity.

DETAILED DESCRIPTION

Definitions

Figure 1:
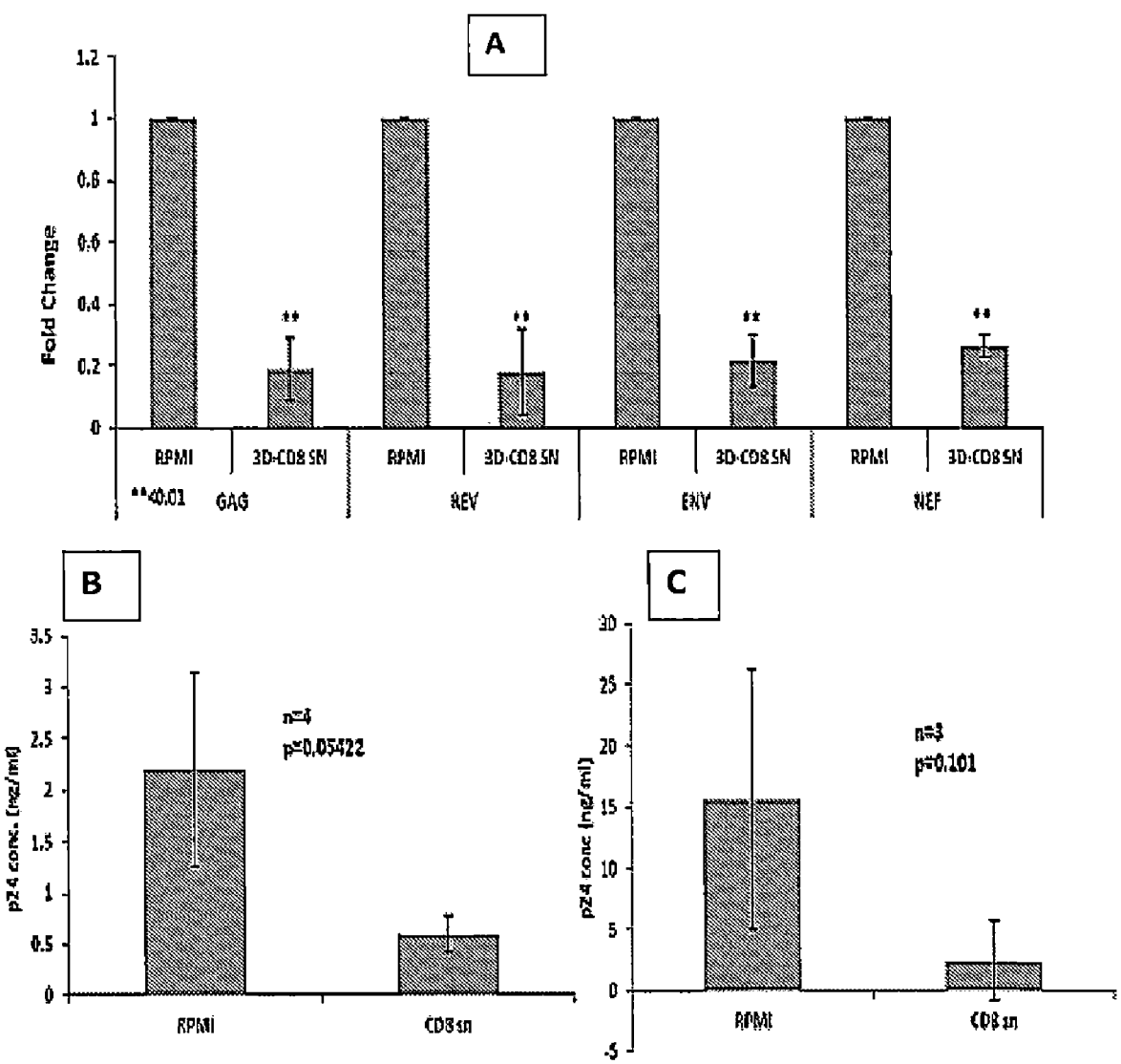
FIG. 1 is a graph showing that 3 Day CD8+ T cell supernatant significantly inhibits HIV infection in infected CD8 depleted PBMCs via: (A.) Real time PCR for viral proteins as well as: (B.) TZM-bl assay of supernatant collected from infected CD8 depleted PBMCs that were infected with HIV and then incubated for 3 days with CD8+ T cell supernatant and (C.) p24 ELISA.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

The terms "synergy", "synergism" or "synergistic" mean more than the expected additive effect of a combination. A synergistic effect may be attained when the active ingredients are: (1) co-formulated and administered or delivered simultaneously in a combined, unit dosage formulation; (2) delivered by alternation or in parallel as separate formulations; or (3) by some other regimen.

The term "subject" as used herein, refers to a human or veterinary subject, preferably a human subject.

The term "therapeutic effect" as used herein means an effect which induces, ameliorates or otherwise causes an improvement in the pathological symptoms, disease progression or physiological conditions associated with or resistance to succumbing to a disorder, for example restenosis, of a human or veterinary subject. The term "therapeutically effective amount" as used with respect to a drug means an amount of the drug which imparts a therapeutic effect to the human or veterinary subject.

Methods of Treating a Viral Infection

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of assay methods, methods of analysis, or other aspects, are disclosed. It is to be understood that each such disclosed feature or features can be combined with the generalized features discussed, to form a disclosed embodiment of the present invention.

One aspect of the present invention provides methods of treating a viral infection by administrating a therapeutically effective amount of at least one Wnt ligand protein, or a pharmaceutical composition including a least one Wnt ligand protein to a subject in need of such a treatment. The viral infection can be, for example, an HIV infection, an Human Hepatitis Virus (HCV), a Cytomegalovirus infection or a Sendai-Virus infection. In one preferred embodiment, the method is used to treat an HIV infection. In such an embodiment, the Wnt ligand protein may suppress HIV replication at the level of transcription and/or a different stage in viral life cycle.

In various embodiments of the present invention, the Wnt ligand protein is Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 or Wnt16. The method of the invention can include the administration of 1, 2, 3, 4, 5, 6, 7, 8, 9, 10 or more of these proteins. In certain embodiments, the method includes the method includes the administration at least one Wnt ligand protein from the group Wnt1, Wnt2B, Wnt6, Wnt7A, Wnt7B, Wnt10A and Wnt16 or from the group Wnt1, Wnt2B, Wnt3, Wnt5B, Wnt8A, Wnt9A, Wnt9B, Wnt10A, Wnt10B and Wnt16. In other embodiments, the method includes the administration of 2, 3, 4, 5, 6 or 7 Wnt ligand proteins from this group. These proteins can be administrated simultaneously, for example, the proteins can be present in a single pharmaceutical composition that is administrated to the subject. Alternatively, one or more of these proteins can be present in different compositions that are administrated separately.

The method can include the administration of 2, 3, 4, 5, 6 or more of the Wnt ligands to produce a synergistic effect in reducing viral replication. In such embodiments, the combination of at least two Wnt ligand proteins is more effective than the additive effects of the individual proteins. In one embodiment, the method includes the administration of a composition including a therapeutically effective amount of a combination of Wnt 1 and Wnt 7a. In another embodiment, the composition is a synergistic combination of Wnt 1 and Wnt 7a.

A composition including at least one Wnt ligand protein can also be administered along with another antiviral agent, For example, then the method is used to treat an HIV infection, the least one Wnt ligand protein can be administered in combination with a reverse transcriptase inhibitor or a protease inhibitor. Such combination can also be used to produce a synergistic effect on viral replication. In certain embodiments, the use of the above combinations can allow for a reduction in the therapeutically effective dose of one or more of the drugs in the combination. Such a reduction can result in the reduction in harmful side effects. In other embodiments, a Wnt ligand protein in used to treat an HIV infection that is resistant to a reverse transcriptase inhibitor or a protease inhibitor.

In one embodiment, the Wnt ligand protein is a Wnt ligand protein secreted a CD8 T cell. In such an embodiment, the composition can be prepared by a method including contacting a CD8 T cell with anti-CD3/CD28. For example, the Wnt ligand protein can be prepared by a method including contacting a CD8 T cell with anti-CD3/CD28. β-catenin is a restriction factor for HIV transcription in astrocytes, and CD4+ T cells, and in the case of monocytes regulates their susceptibility to HIV infection. The observation that β-catenin inhibits HIV transcription is reminiscent of CD8 Cell Non-cytotoxic Antiviral Response (CNAR). In CNAR, CD8+ T cells secrete a yet to be identified entity referred to as CD8 antiviral factor (CAF) that inhibits LTR-driven transcription of the HIV provirus in CD4+ T cells. The identity of CAF has remained elusive for over 30 years. The present inventor has identified CAF as a Wnt ligand on the basis of the numerous parallels can be drawn between Wnt ligands and CAF. Both Wnt ligands are small secreted proteins. Once in contact with CD4+ T cells, Wnt ligands trigger intracellular signaling pathways that culminate in activation of transcription factor(s) which inhibit HIV proviral transcription. Also, their activity is non-cytotoxic, CAF activity actually appears to maintain CD4+ T cell survival and Wnts stabilize β-catenin which is a pro-survival protein. Furthermore, the present disclosure demonstrates that Wnt ligands are secreted by CD8+ T cells and when removed from CD8 conditioned media, CNAR activity is lost. Additionally, antagonizing Wnt signaling in HIV infected CD4+ T cells by adding Dickkopf-1protein (DKK-1) abrogates CNAR activity. Lastly, Wnts 1 and 7a added to infected CD4+ T cells also inhibit HIV.

Another aspect of the present invention provides a method of boosting the level of HIV replication from a latent reservoir of HIV. HIV is able to remain a chronic infection due to its ability maintain reservoirs within infected blood cells. Such reservoirs are not accessible to the body's immune defenses, nor are they sensitive to anti-HIV drugs. Latent reservoirs of HIV are located throughout the body, including the brain, lymphoid tissue and bone marrow, and persist even in the presence of antiretroviral therapy.

In one embodiment, the level of HIV replication in the latent reservoir is boosted by the administration of a drug that suppresses the level of Wnt ligands. For example, such a drug can be administered in the presence of an antiretroviral agent, such as a nucleoside or a non-nucleoside reverse transcriptase inhibitor, a protease inhibitor, an entry inhibitor or an HIV integrase inhibitor. As the reservoirs begin producing HIV, the infected cells will be recognized and attacked by the immune system. The HIV virus will also be more susceptible to attached by the antiretroviral agent. The level of Wnt ligands can be suppressed by the administration of a drug such as Dickkopf-related protein.

Drug Combinations

Another aspect of the present invention provides a drug combination including at least two Wnt ligand proteins from the group Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 and Wnt16. In one embodiment, the drug combination is a synergistic drug combination where the Wnt ligand proteins are present in synergistically effective amounts.

For example, the drug combination can be a synergistic combination of Wnt 1 and Wnt 7a. In one embodiment, the synergistic drug combination is synergistically effective in treating a HIV viral infection. The drug combination may also include a pharmaceutically acceptable carrier, diluent or excipient.

Pharmaceutical Compositions

Another aspect of the present invention provides pharmaceutical compositions including at least one of the Wnt ligands disclosed above and a pharmaceutically acceptable carrier, diluent or excipient. For example, the pharmaceutical composition may include 1, 2, 3, 4, 5 or more of such Wnt ligand(s.) The pharmaceutical compositions can be in the form of, for example, tablets, pills, dragees, hard and soft gel capsules, granules, pellets, aqueous, lipid, oily or other solutions, emulsions such as oil-in-water emulsions, liposomes, aqueous or oily suspensions, syrups, elixiers, solid emulsions, solid dispersions or dispersible powders. In pharmaceutical compositions for oral administration, the agent may be admixed with commonly known and used pharmaceutically acceptable carriers, diluents or excipients, for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. GELUCIRE). In the pharmaceutical composition, the agent may also be dispersed in a microparticle, e.g. a nanoparticulate, composition.

For parenteral administration, the agent or pharmaceutical compositions of the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally, for parenteral administration the agent or pharmaceutical compositions of the agent can be in the form of an aqueous, lipid, oily or other kind of solution or suspension or even administered in the form of liposomes or nano-suspensions.

Modes of Administration

The Wnt ligands or pharmaceutical compositions including the Wnt ligands can be administered by any method that allows for the delivery of a therapeutic effective amount of the agent to the subject. Modes of administration can include, but are not limited to, oral, topical, transdermal and parenteral routes, as well as direct injection into a tissue and delivery by a catheter. Parenteral routes can include, but are not limited to subcutaneous, intradermal, intravenous, intraperitoneal and intramuscular routes. In one embodiment, the route of administration is by topical or transdermal administration, such as by a lotion, cream, a patch, an injection, an implanted device, a graft or other controlled release carrier. Routes of administration include any route which directly delivers the composition to the systemic circulation (e.g., by injection), including any parenteral route.

One embodiment of the method of the present invention comprises administering at least one Wnt ligand, in a dose, concentration and for a time sufficient to a treat viral infection in a subject. Certain embodiments include administering at least one Wnt ligand in a dose between about 0.1 micrograms and about 100 milligrams per kilogram body weight of the subject, between about 0.1 micrograms and about 10 milligrams per kilogram body weight of the subject, between about 0.1 micrograms and about 1 milligram per kilogram body weight of the subject. In practicing this method, the Wnt ligand or therapeutic composition containing the agent can be administered in a single daily dose or in multiple doses per day. This treatment method may require administration over extended periods of time. The amount per administered dose or the total amount administered will be determined by the physician and will depend on such factors as the mass of the patient, the age and general health of the patient and the tolerance of the patient to the compound.

Embodiments of the invention will be further described in the following examples, which do not limit the scope of the invention described in the claims.

EXAMPLES

Example 1

Production of SC8 Anti-Retroviral Factor ("CAF")

The CD8+ T cells, as well as CD8 depleted peripheral blood mononucleated cells (PBMCs), were cultured in complete RPMI medium containing heat-inactivated fetal calf serum, L-glutamine, penicillin, streptomycin, IL-2, anti CD3 and anti CD28 for 72 hours after which cells were centrifuged and the supernatant was collected. The cells were used immediately or were stored at −80° C. for future use. Multiple Freeze/thaw cycles do not affect CAF activity.

After 72 hours of activation the CD8 depleted PBMCs were infected with 2 ng/1 million cells HIVBal overnight, washed, and incubated with 3 day CD8+ T cell supernatant between 3 and 6 days before HIV inhibition was measured by one or a combination of the three methods: real time PCR, TZM-bl assay and p24 ELISA. Regardless of the method used, CD8+ T cell supernatant is a potent inhibitor of HIV (FIG. 1).

Example 2

Expression of Wnt Ligands by CD8 T Cells

Figure 2:
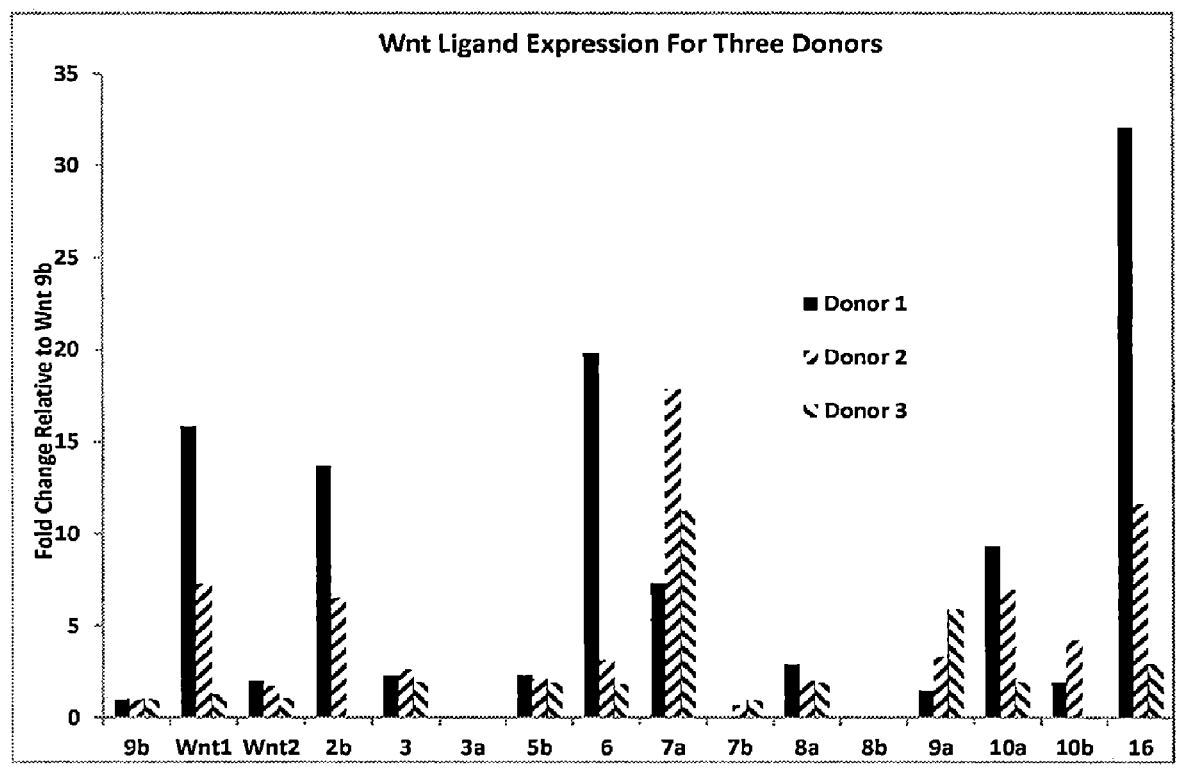
FIG. 2 is a graph showing that the CD8 T cells express distinct Wnt ligands. CD8 T cells were stimulated with anti-CD3/CD28 from three different healthy donors and expression of Wnt ligands was measured by real-time RT-PCR and data normalized to GAPDH.

CD8 T cells were stimulated with anti-CD3/CD28 from three different healthy donors. Expression of Wnt ligands was measured by real-time RT-PCR and data normalized to GAPDH. FIG. 2 shows that the CD8 T cells express distinct Wnt ligands.

Example 3

Abrogation of CAF Activity by Dickkopf-related Protein 1(DKK1)

Figure 3:
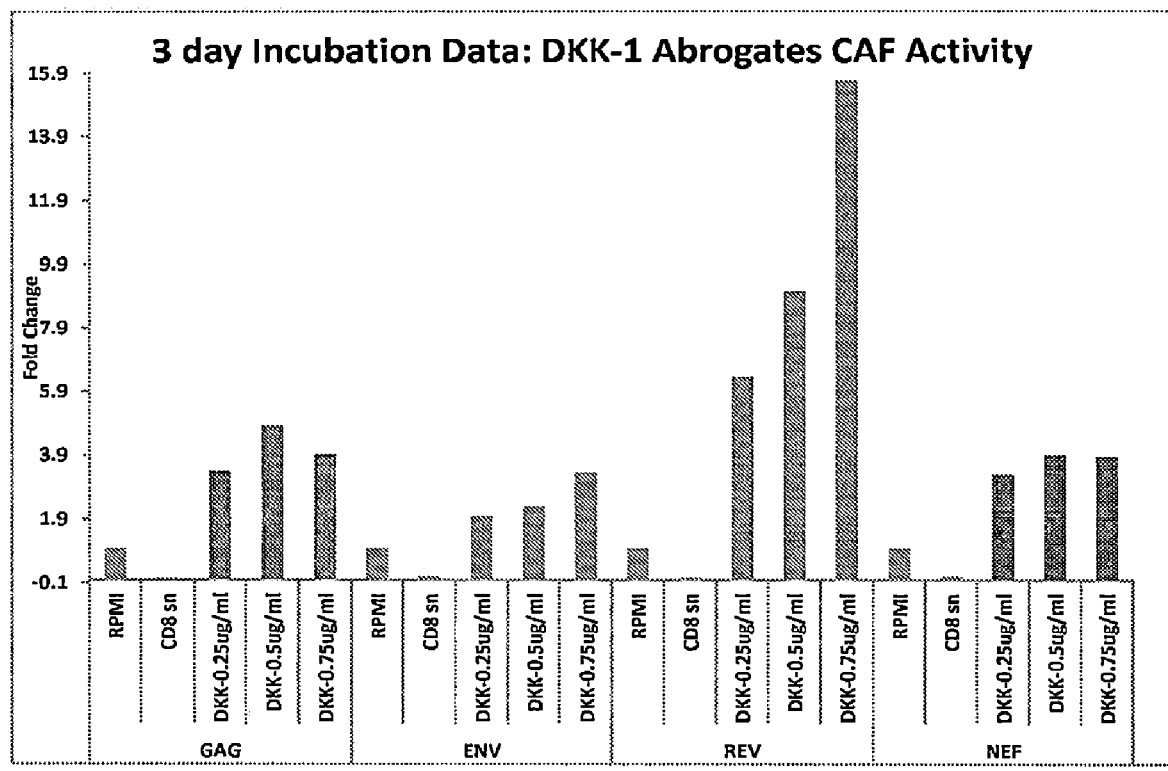
FIG. 3 is a graph showing the abrogation of CAF activity by Dickkopf-related Protein 1(DKK1.) Supernatant from CD8 T cells harboring CAF activity is incubated with varying concentrations of DKK1.

Supernatant from CD8 T cells harboring CAF activity is incubated with varying concentrations of DKK1. Both Wnt ligands and DKK1 bind to LRP receptors on cells. DKK1 competes with Wnt ligands for LRP binding. DKK1 is shown to abrogate the ability of supernatant from CD8 T cells to suppress HIV replication in CD4+ T cells (FIG. 3.) HIV replication was evaluated by measuring HIV gag, env, rev, and nef mRNAs.

Example 4

Removal of Wnt ligands from supernatant of CD8 T cells harboring CAF abrogates their ability to suppress HIV. Currently there are no neutralizing antibodies for Wnt ligands and many of the antibodies seem to be cross-reactive. We depleted CAF supernatant of Wnt 1, 2, 6, and 16 by a magnetic bead protocol. Briefly, Pierce Protein A/G Magnetic Beads (Life Technologies Invitrogen, Carlsbad, Calif.) were washed two times for 1 hour at 4° C. with 1×GE Binding Washing Buffer (GE Life Sciences, Pittsburgh, Pa.) and coated with 4 µg of anti-rabbit Wnt 1, Wnt2, Wnt 6, or Wnt 16 or rabbit IgG1 isotype control (Abcam, Cambridge, Mass.) for overnight at 4° C. with continuous rotation at 30 rpm. One mL of supernatant from PBMCs was then applied to each of the beads and incubated overnight at 4° C. The supernatant was then collected by separation of magnetic beads under a magnetic field and depletion of Wnts was confirmed by western blot of the supernatant. The Wnt-depleted supernatant was added to HIV infected CD4 T cells. FIG. 4 shows that depletion of these ligands led to an abrogation of CAF activity.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

I claim:

1. A method of treating a viral infection, the method comprising:
   administering to a subject in need of such treatment a composition comprising a therapeutically effective amount of at least one Wnt ligand protein selected from the group consisting of Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 and Wnt16; and
   inhibiting viral transcription.

2. The method of claim 1, wherein the viral infection is a human immunodeficiency virus infection.

3. The method of claim 1, wherein the composition suppresses human immunodeficiency virus replication at the level of transcription.

4. The method of claim 1, wherein the Wnt ligand protein is selected from the group consisting of Wnt1, Wnt2B, Wnt3, Wnt5B, Wnt8A, Wnt9A, Wnt9B, Wnt10A, Wnt10B and Wnt16.

5. The method of claim 1, wherein the composition comprises a therapeutically effective amount of at least two Wnt ligand proteins selected from the group consisting of Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 and Wnt16.

6. The method of claim 5, wherein the composition comprises a synergistic combination of at least two Wnt ligand proteins selected from the group consisting of Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11 and Wnt16.

7. The method of claim 2, wherein the human immunodeficiency virus is resistant to a reverse transcriptase inhibitor or a protease inhibitor.

8. The method of claim 7, wherein the human immunodeficiency virus is resistant to a reverse transcriptase inhibitor.

9. The method of claim 1, wherein the composition further comprises at least one pharmaceutically acceptable carrier, diluent or excipient.

10. The method of claim 1, wherein the subject is a human subject.

11. The method of claim 1, wherein the composition is prepared by a method comprising contacting a CD8 T cell with anti-CD3/CD28.

12. The method of claim 1, wherein the viral infection is selected from the group consisting of an human immunodeficiency virus infection, a Cytomegalovirus infection, an HCV infection and a Sendai-Virus infection.

13. The method of claim 1, wherein the composition comprises a therapeutically effective amount of a combination of Wnt 1 and Wnt 7a.

14. The method of claim 1, wherein the composition comprises a therapeutically effective amount of a synergistic combination of Wnt 1 and Wnt 7a.

* * * * *